United States Patent [19]

Polaschegg

[11] Patent Number: 4,683,053
[45] Date of Patent: Jul. 28, 1987

[54] HEMODIALYSIS DEVICE

[75] Inventor: Hans-Dietrich Polaschegg, Oberursel, Fed. Rep. of Germany

[73] Assignee: Fresenius AG, Bad Homburg, Fed. Rep. of Germany

[21] Appl. No.: 731,808

[22] Filed: May 7, 1985

[30] Foreign Application Priority Data

May 8, 1984 [DE] Fed. Rep. of Germany ....... 3416955

[51] Int. Cl.⁴ ............................................. B01D 13/00
[52] U.S. Cl. .................................. 210/86; 210/321.3; 210/929
[58] Field of Search ................ 210/86, 90, 321.3, 929, 210/137

[56] References Cited

U.S. PATENT DOCUMENTS

| | | | |
|---|---|---|---|
| 3,441,136 | 4/1969 | Serfass et al. | 210/137 X |
| 3,979,284 | 9/1976 | Granger et al. | 210/929 X |
| 4,141,834 | 2/1979 | Bellotti et al. | 210/929 X |
| 4,370,983 | 2/1983 | Lichtenstein | 210/929 X |

Primary Examiner—Frank Spear
Attorney, Agent, or Firm—Townsend and Townsend

[57] ABSTRACT

Hemodialysis device (10) with a control apparatus (74) and a line (52) which is connected to a valve arrangement (50) downstream of the suction pump (20) and to a dialyzing liquid source (16). The dialyzing liquid source (16) has a volume measuring apparatus (54, 58) with which the ultrafiltrate generated by the suction pump (20) can be determined in the recirculation circuit. The ultrafiltration rate thereby established serves to control the suction pump (20) with the aid of the control apparatus (74), in some cases the transmembrane pressure being determined with the aid of the pressure gauges (62, 66) and from which the current ultrafiltration coefficient can be measured. Furthermore, the hemodialysis device (10) has a safe possibility of feeding disinfectant concentrate into the recirculation circuit downstream of the dialyzer (12).

7 Claims, 1 Drawing Figure

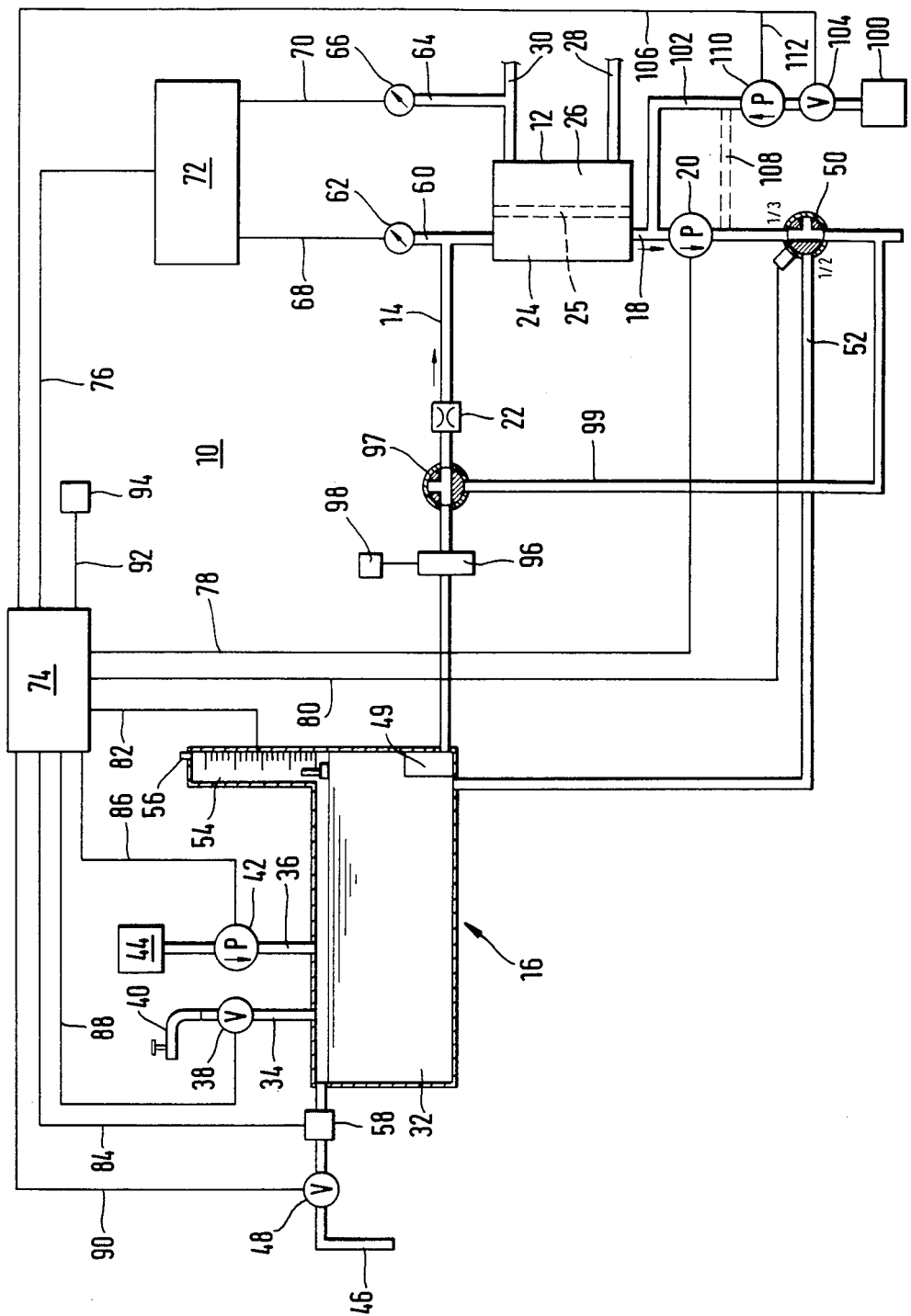

HEMODIALYSIS DEVICE

BACKGROUND OF THE INVENTION

The invention relates to a hemodialysis device with a dialyzer which has two chambers separated by a membrane, of which one is switched into a dialyzing liquid path and the other into a blood path, with a dialyzing liquid source, with a suction pump arranged in the dialyzing liquid path and controlling the transmembrane pressure, with a restrictor apparatus arranged upstream of the dialyzer in the dialyzing liquid path, with a change-over valve interposed downstream of the suction pump in the dialyzing liquid path, with a line going off from the change-over valve and returning to the dialyzing liquid path upstream of the dialyzer, with a volume measuring apparatus connected to the dialyzing liquid path for measurement of the volume of the ultrafiltered liquid quantity, with an apparatus for determination of the transmembrane pressure in the dialyzer and with a control apparatus which is connected to the unit for determination of the transmembrane pressure and controls the suction pump.

The homodialysis device mentioned at the start, or artificial kidney, is intended to remove substances normally contained in the urine and to regulate the liquid, electrolyte and acid-base equilibria.

Even if there are initial moves to perform this regulation on the basis of objective, physiological parameters which can be measured continuously, for example by continuous measurement of the hematocrit in the extracorporeal circulation, dialysis is still craried out today exclusively on the basis of empirically established ideal or set values (cf. ASAIO 7 (1983), p. 410). The bulk of the units in use today do not even allow the parameters given by the physician to be maintained precisely, let alone allow specific control of these units.

An area in which certain progress has been made is in the field of ultrafiltration control, in which to an increasing extent so-called volume-controlled dialysis units are being used, which allow an exact ultrafiltration, provided that certain preconditions are met regarding the technical aspects of the apparatus. In the case of such devices, ultrafiltration is performed in a closed volume of dialyzing liquid which is periodically changed. Only in such a closed system, of which the A 2008 C dialysis unit of the applicant is an actual example, is it ensured that accurate ultrafiltration control can be carried out.

On the other hand, for reasons of cost, in many countries simple single-pass units are still in use which currently cannot be changed although the advantages of volume-controlled devices for the patient are sufficiently demonstrated and recognized.

Consequently, it has been necessary to develop devices through which the known simple hemodialysis devices can be verified and adjusted.

The transfer of liquid from the blood circuit to the dialyzing liquid circuit, ie. the ultrafiltered liquid, can be performed by devices both on the blood side and on the dialyzing liquid side. The following processes for this are known:

As already mentioned above, a volume control can be ensured by a balancing device, which ensures that the liquid quantities flowing to and from the dialyzer are equal. The quantity to be ultrafiltered is withdrawn from this balancing device by an additional apparatus, namely an ultrafiltrate pump, so that finally the ultrafiltrate can be determined exactly. Such a device is known for example from German Offenlegungsschrift No. 28 38 414.

Furthermore, a relative flow measurement of the liquid quantities flowing to and from the dialyzer, ie. the quantities of blood or in particular dialyzing liquid, can be performed. By use of the properties of difference formation per unit of time, comparison with a pre-set rate and control of the transmembrane pressure, the desired rate can be achieved. This principle is realized, for example, on the dialyzing liquid side by the UFM-2 ultrafiltration module of the Gambro Company. For the blood side, such a device is specified in German Auslegeschrift No. 33 13 421.

Another process comprises measuring the ultrafiltration coefficient. As is known, this changes from dialyzer to dialyzer due to deviations of a technical production nature and in particular during the course of dialysis, since the membranes change or the pores become blocked. Consequently, the ultrafiltration quantity also changes, regularly becoming less per unit of time in the course of dialysis. Therefore, the ultrafiltration coefficient must be determined discontinuously in the course of dialysis, keeping this measuring period of the transmembrane pressure TMP constant. This is the case with the hemofiltration units COBE CENTRY 2000 or Braun UF Module.

On the other hand however, the ultrafiltration rate can be given and the self-adjusting mean TMP becoming can be From the UF rate and the TMP in turn, the UF coefficient can be calculated and consequently the TMP can be controlled in such a way that the preset UF rate is attained.

German Patent Specification No. 25 48 759 discloses a dialysis unit with which the ultrafiltration rate can be measured at any time during the blood dialysis treatment and the dialysate pressure can be kept at a value which is adapted to a pressure adjusted in the dialyzer. This arrangement works with a pump in both the supply line and in the discharge line of the dialyzing liquid, these pumps being driven by a common motor and having the same displacement capacity.

Apart from the fact that this arrangement requires highly elaborate apparatus, in addition it is also not adequately accurate as such pumps have an error in their displacement capacity of about 2%. If the thought is considered that about 2% of the dialyzing liquid quantities flowing through the dialyzer are additionally to be withdrawn as ultrafiltration quantity, it is already apparent that no accurate ultrafiltration can be carried out with such an arrangement and in some cases the use of such an arrangement may even be critical for the patient.

German Offenlegungsschrift No. 32 02 831 discloses a hemodialysis device of the type first mentioned above in which the open circuit in a single-pass device is closed for the duration of measurement of the withdrawn ultrafiltrate quantity and the withdrawn ultrafiltrate quantity is determined in a volume measuring apparatus as a function of the measuring period. The known dialysis apparatus is disadvantageous inasmuch as it requires a highly elaborate apparatus to be able to determine this measured value exactly. This results in a possibility of error accumulation, so that it is desirable to use a less error-susceptible device.

In the hemodialysis device according to German Offenlegungsschrift No. 32 02 831, this disadvantage results initially from the fact that a further pump has to be provided in the dialyzing liquid source, absolutely necessary for displacing the dialyzing liquid into the dialyzing liquid circuit. If, for example, a dialyzing liquid of incorrect composition is produced, a dialysis unit usually has a protective system which takes care that the dialyzing liquid of incorrect composition is displaced past the dialyzer into a bypass line into the drain.

Furthermore, this known dialysis device has a displacement pump in connection with a restrictor which is designed as a constant flow apparatus and which is intended to adjust a certain transmembrane pressure in conjunction with the suction pump arranged downstream of the dialyzer. Due to the usual rate of inaccuracy of about 2% which can be established for such a pump, such a device must be switched to measuring operation relatively frequently, which leads to interruption of treatment of the patient. Added to this is that, with an increasing number of pumps used in such a dialysis device and number of valve arrangements, the error susceptibility and the inaccuracy of such a hemodialysis device increases, which is undesirable.

Furthermore, in this known hemodialysis device, the volume measuring apparatus branches off directly from the dialyzing liquid circuit downstream of the dialyzing liquid source, which has the disadvantage during a relatively long measuring period that the dialyzing liquid cools down, with the consequence that the patient may freeze to death during dialysis treatment.

German Offenlegungsschrift No. 23 28 593, corresponding to U.S. Pat. No. 3,979,284 to Granger et al., and German Offenlegungsschrift No. 13 29 26 681 disclose hemodialysis devices in which the dialyzing liquid circuit is completely closed for determination of the transmembrane pressure at a certain ultrafiltration rate, an exactly volumetrically working pump being connected to this closed circuit. This additional pump initially increases the costs and the error susceptibility of such a device. Measurement of the transmembrane pressure is made in this case using a given pump rate with which then in turn a further pump, acting as suction pump, is controlled.

In general, the known hemodialysis devices have the disadvantage that they have a separate disinfection program to prevent the patient being connected unintentionally to the disinfectant solution, with fatal effect. Consequently, the known devices have manually fitted dialysis plugs which, once the dialysis device has been switched off, have to be plugged into appropriate sockets in the dialysis device in order to disinfect the entire device.

SUMMARY OF THE INVENTION

The invention is therefore based on the object of developing a hemodialysis device in such a way that the complexity of apparatus for determination of the ultrafiltration rate as a function of the transmembrane pressure is as low as possible.

The object is achieved by connecting the line branching off from the change-over valve to the dialyzing liquid source.

The dialysis device according to the invention has first of all the advantage that a usual singoe-pass dialysis device can be converted without major modification. All that is required is to connect the dialyzing liquid source, in particular the mixing chamber of the dialyzing liquid source, via a connecting line to the dialyzing liquid discharge line downstream of the suction pump, to form a recirculation circuit.

This recirculation circuit is moreover provided with a volume measuring apparatus which is open to the atmosphere in the recirculation phase. This volume measuring apparatus is advantageously likewise connected to the dialyzing liquid source, in particular to the mixing chamber of the dialyzing liquid source, and determines the ultrafiltration quantity withdrawn from the blood circuit as a function of time.

Compared with the known dialysis devices, the hemodialysis device according to the invention has, in particular, the advantage that no further pumps are necessary compared with the usual single-pass device. To this extent, the usual single-pass device must therefore only be equipped with a change-over valve arranged downstream of the suction pump, a connecting line to the dialyzing liquid source and a volume measuring apparatus, which is likewise advantageously connected to the dialyzing liquid source. However, all known dialysis devices have, in comparison, additional pumps which in some cases even have to work volumetrically accurately, and additional valve means which have the disadvantages described above in the determination of this ultrafiltration rate.

By contrast, with the device according to the invention, the ultrafiltration rate can be determined as a function of the transmembrane pressure with a minimum of equipment.

This ultrafiltration rate is input as an actual value into the control apparatus, which controls the suction pump correspondingly on the basis of the set value input at the start of dialysis, in other words on the basis of the ultrafiltered quantity during dialysis. Thus, by increasing the speed of the suction pump, the TMP, and thereby the ultrafiltration rate which is substantially proportionate to the TMP, is increased. On the other hand, the suction capacity, in other words the rotational speed the suction pump, can be reduced, with the consequence that the TMP, and thereby the ultrafiltration rate, drops. Usually however, due to the deterioration in ultrafiltration rate which occurs during dialysis, the suction capacity of the suction pump is increased in order to achieve the predetermined ultrafiltration rate again.

According to a further embodiment, the ultrafiltration coefficient may be determined from the UF rate and the TMP. For this, the mean TMP is established with the aid of pressure pick-ups which are arranged on the blood side and the dialyzing liquid side. The actual UF coefficient is then compared in the control apparatus with the originally measured UF coefficient, ie. measured at the start of dialysis, and adapted to this value by changing the pressure, ie. the speed of the suction pump.

According to a further embodiment, the line connecting the dialyzing liquid source to the drainage line can be provided as a recirculation line for a disinfectant solution. This is fed into the drainage line between the suction pump and the dialyzer with the aid of a feed line, which is constantly connected to a disinfectant concentrate container. This feed line is closed with the aid of a shut-off element which is only opened when the hemodialysis unit is switched to the disinfection program.

This process is to be regarded as safe in accordance with the guidelines for medical-technical devices, as at least two errors have to occur to produce a dangerous situation. For instance, the unit would have to go into recirculation unintentionally, which is easy to measure as the net water supply stops, and the disinfectant valve would have to be opened simultaneously.

According to a further advantageous embodiment, the disinfectant feed line may also be connected downstream of the suction pump to the dialyzing liquid discharge line, so that the disinfectant is fed in the overpressure region. In the event that the above mentioned valve in the disinfectant line were to leak, an intake of disinfectant would also be excluded in this case as the overpressure downstream of the suction pump would prevent this. To overcome this pressure, a separate pump is provided in the line for the feed of the disinfectant concentrate, so that this makes the system even more safe.

Further features, details, and advantages of the invention are explained in the following description of exemplary embodiments with reference to the drawing.

BRIEF DESCRIPTION OF THE DRAWING

The FIGURE diagrammatically shows an embodiment of the hemodialysis device according to the invention.

DESCRIPTION OF THE SPECIFIC EMBODIMENTS

The FIGURE reveals, at 10, a hemodialysis device which consists of a dialyzer 12, which is connected via a supply line 14 to a dialyzing liquid source 16. At the outlet of the dialyzer 12 is connected a drainage line 18 in which a suction pump 20 is interposed.

Also interposed in the supply line 14 is a restrictor 22 which is advantageously set at a fixed constriction. Also provided in the supply line 14 is a device for venting the dialyzing liquid (not shown).

The dialyzing liquid source 16, the supply line 14 and the discharge line 18 form, together with the chamber 24 of the dialyzer 12, a dialyzing liquid path through which the dialyzing liquid flows. Through the other chamber 26, which is separated from the chamber 24 by the membrane 25, flows blood, and for this purpose it is connected to a supply line 28 and a discharge line 30.

The dialyzing liquid source 16 consists according to the embodiment shown in the figure of a mixing chamber 32, into which lead a line 34 for the feeding of fresh water and at least one line 36 for the feeding of a concentrate. For this purpose, the line 34, in which a valve 38 is interposed, is connected to a fresh water connection 40, while the line 36, in which a concentrate pump 42 is interposed, is connected to at least one concentrate container.

Furthermore, the mixing chamber 32 has on its upper side a discharge line 46, through which the overflowing dialyzing liquid can drain. In this discharge line 46 is provided a valve 48.

Such a mixing chamber 32 in conjunction with these feed and disposal lines is known, so that the description of the dialyzing liquid itself is dispensed with.

The mixing chamber 32 has at its transition to the supply line 14 a degassing and displacement apparatus 49, in which usually a restrictor and a pump are provided, the latter displacing the degassed dialyzing liquid into the supply line 14.

The discharge line 18 has downstream of the suction pump 20 a valve arrangement 50, which in the ½ position connects the drainage line 18 directly to the drain, while in the ½ position it connects the drainage line 18 via a line 52 to the dialyzing liquid source 16, in particular to the mixing chamber 32. The line 52 advantageously opens out near to the bottom of the mixing chamber 32.

The upper side of the mixing chamber 32 has according to the embodiment shown in the figure a volume measuring apparatus 54, which is advantageously pressure-equalized via a venting orifice 56. This venting orifice 56 can be closed with an air-permeable sterile membrane.

Suitable as volume measuring apparatuses are all known liquid measuring apparatuses which work volumetrically, in other words a level tube with float arrangement, ultrasonic level measuring devices, light barriers which monitor the level meter, and the like.

According to a further embodiment, instead of this first volume measuring apparatus 54, a second volume measuring apparatus 58 can be provided in the discharge or overflow line 46. In this case, the volume measuring apparatus 58 is advantageously designed as a flow meter or a turbine which determines the overflowing dialyzing liquid quantity, and—as explained below—the valve 48 in the overflow line 46 is no longer necessary and can thus be omitted.

According to a further advantageous embodiment, the feed line 14 is connected via a line 60 to a pressure gauge 62 for determination of the pressure in the chamber 24 of the dialyzer 12 through which the dialyzing liquid flows, while the blood line 30 is connected via a line 64 to a further pressure gauge 66. These pressure gauges 62 and 66 are connected via electrical lines 68 and 70 to a pressure evaluation unit 72, with which the transmembrane pressure TMP at the membrane 25 is determined by formation of the difference between the pressure values given by the pressure gauges 62 and 66.

The pressure gauge 62 may optionally also be arranged downstream of the dialyzer 12. Also, an embodiment is possible in which a pressure gauge 62, 66 is arranged both downstream and also upstream of the dialyzer 12 in the blood circuit and/or in the dialyzing liquid circuit, to make possible in this way a determination, and in some cases control, of the means TMP (see DIN 57750, part 1206).

The hemodialysis device 10 has, furthermore, a control apparatus 74, which is connected via an electrical line 76 to the pressure evaluation unit 72. Furthermore, the control apparatus 74 is connected via an electrical line 78 to the suction pump 20, a line 80 is connected to the valve arrangement 50, a line 82 is connected to the volume measuring apparatus 54 and a line 84 to the volume measuring apparatus 58, an electrical line 86 to the concentrate pump 42, a line 88 to the valve 38 in the fresh water line 34 and an electrical line 90 to the valve 48 provided in the discharge line 46. The control apparatus 74 is advantageusly connected via a further electrical line 92 to a set value input apparatus 94.

In the control apparatus 74, initially the ultrafiltrate quantity to be drawn off, in particular the ultrafiltration rate, is adjusted with the aid of the set value input apparatus 94. As, in the case of the dialyzers used, the ultrafiltration coefficient is regularly known at the start of dialysis, and, in some cases, can likewise be input into the control apparatus 74 via the set value input apparatus 94, the dialysis device 10 can be started up without difficulties by regulating the TMP with the aid of the suction pump, as the ultrafiltration rate corresponds to a certain TMP.

Once the hemodialysis device 10 is in operation, further control of the pump 20 is performed at regular intervals, ie. after about 10–30 minutes in accordance with the process described below.

If the ultrafiltration rate is to be verified, the control apparatus 74 initially switches the valve arrangement 50 over from the ⅓ position to the ½ position via the line 80. At the same time, the valve 48 in the discharge line 46 is closed, provided that the volume measuring apparatus 54 is used. If this is not the case, the volume measuring apparatus 58 is activated instead of the volume measuring apparatus 54.

In the preferred embodiment, the TMP is input via the line 76 into the control apparatus 74, while the measured volumes in the volume measuring apparatuses 54 and 58 are likewise input into the control apparatus 74 as a function of time. At the start of the determination, the fresh water supply and the concentrate feed are interrupted. the former by closing the valve 38 and the latter by switching off the pump 42.

In the circulation circuit thereby formed, the ultrafiltrate generated by the under-pressure in the under-pressure section between the restrictor 22, the dialyzer 12 and the suction pump 20 and constituting an excess quantity in the recirculation circuit formed is either carried away via the overflow 46 or pumped into the volume measuring apparatus 54 designed as a riser.

In these two volume measuring apparatuses 54 and 58 is performed determination of the ultrafiltrate quantity, the value of which as a funciton of time is compared as an actual value with the input set value in the control apparatus 74. Whenever these values do not agree, the suction pump 20 is adjusted with the aid of the control apparatus 74.

In a further embodiment, the TMP is additionally stored during this measurement in the control apparatus 74 and the ultrafiltration coefficient is determined from the quotient of ultrafiltration rate and TMP. This can be compared in a corresponding way with the ultrafiltraton coefficient registered at the start of dialysis, the deviation from the original value acting as a parameter for controlling the TMP.

Once the ultrafiltration rate has been regulated to the predetermined value, the valve arrangement 50 is moved to the ⅓ position, the valves 38 and 40 opened and the concentrate pump 52 actuated again. At the same time, the control apparatus 74 is disconnected from the measured value transmitters.

During the measurement, the TMP of course remains constant, ie. the displacement capacity of the suction pump 20 is not changed during the measuring time. Should this not be sufficient, the transmembrane pressure is advantageously adjusted to the constant value with the aid of the pressure gauges 62 and 66, the pressure evaluation unit 72 and the control apparatus 74, the control apparatus performing control of a constant TMP at the pump 20.

For ultrafiltration quantity measurement with isolated ultrafiltration, a measuring vessel can be connected to the overflow 46. It is then constantly rinsed with warm, but recirculating dialyzing liquid during the isolated ultrafiltration of the dialyzer 12, thus preventing cooling off. This isolated ultrafiltration is usually operated without dialyzing liquid flow to avoid a diffusion of electrolytes. The same aim is achieved with the recirculation with the above device.

As mentioned above, the recirculation causes an electrolyte balance to be produced between blood and the recirculating dialyzing liquid, so that the concentration of the electrolytes in the dialyzing liquid assumes a value at which there is no longer any net electrolyte transfer from the blood into the dialyzing liquid and back. The conductivity of the fresh dialyzing liquid and that of the recirculating dialyzing liquid can then be used to reach a conclusion regarding electrolyte transfer during the dialysis, which is an advantageous side effect of the device according to the invention. This can be measured, for example, by a conductivity meter 96, which is provided in the supply line 14 and displayed in an indicating device 98, which is connected to the conductivity meter 96.

Interposed in the supply line 14 downstream of the conductivity meter 96 is a bypass valve 97, from which a bypass line 99 goes off, which is connected to the discharge line 18. Whenever the conductivity meter detects a dialyzing liquid of incorrect composition, the bypass valve 97 switches into the bypass operation and the dialyzing liquid of incorrect composition is displaced past the dialyzer 12 directly into the discharge by the action of the displacement apparatus 49.

According to a further advantageous embodiment, a disinfectant concentrate can be fed directly to the hemodialysis device 10 from a container 100. This container 100 is connected via a line 102 to the drainage line 18 upstream of the suction pump 20.

Interposed in the line 102 is a valve 104 which can only be opened during a disinfection program.

This disinfection program is carried out with the aid of a control device, which may be united, for example, with the control apparatus 74. It can switch and control the valve 104 via the line 106 and—as mentioned above—the valve 50, the water inlet valve 38, in some cases the valve 48 and the pump 42.

For disinfection of a machine previously flushed with water, the valve 50 is initially switched to the ½ position, the water inlet valve 38 and, in some cases, the valve 48 are closed and the concentrate pump 42 stopped. The suction pump 20 is controlled in such a way that an underpressure of typically 50–100 mbar is produced on the intake side. Subsequently, the valve 104 is open long enough for a quantity of disinfectant concentrate corresponding to the required concentration to be sucked in then is subsequently closed. This concentrate quantity is mixed and pumped round (recirculated) with even distribution and for a time corresponding to the necessary action time.

However, it is also possible to switch the unit off after a short forced recirculation phase, which serves to intermix concentrate and water, and to wait for a generally extended disinfection in period state of rest.

At the end of the disinfection phase, the valve 50 is again switched to the ⅓ position and the valves 38 and 48 opened. Subsequently, the machine is flushed.

The opening time of the valve 104 is determined empirically. With usual concentrates, which have to be diluted 1:34, the necessary quantity of concentrate is obtained from the filling volume of the dialyzing liquid circuit of the hemodialysis device 10 divided by 34.

If, instead of the valve 104, or in addition to it, a pump 110 is provided, this quantity can be displaced adequately accurately without any difficulty by corresponding control of this pump 110.

Dialysis can subsequently be performed again.

As already mentioned above, even this arrangement is safe from a first error. However, in order to improve the safety still further, the line 102 is connected via the line 108, drawn in broken lines, to the discharge line 18 downstream, and not upstream of the suction pump 20, and is thus located in the overpressure region, so that even with an unintentionally opened valve 104 no disinfectant concentrate can get into the recirculation circuit. To overcome this over-pressure, a pump 110 is provided in the line, which pump is actuated only during the disinfection program, but otherwise, like the valve 104, blocks the line 102. This pump is likewise connected via an electrical line 112 to the line 106 and is thus actuated by the control apparatus 74, in conjunction with the valve 104.

The recirculation provided according to the invention makes possible the following disinfection process:

1. The hemodialysis unit 10 is flushed by water flowing through (without recirculation).
2. Subsequently, it is switched to the disinfection program, the recirculation circuit being set up—as explained above. This is followed by the feeding of the disinfectant concentrate from the container 100 into the recirculation circuit. A certain quantity is introduced, which is adequate to bring the concentration of the disinfectant to the required level in the entire circuit.
3. After a waiting time, which can last up to the next treatment, the unit is automatically flushed. This involves relinquishing the recirculation and flushing with water.

This process is more safe because the disinfectant is fed downstream of the dialyzer 12 and cannot reach the dialyzer 12 again until recirculation. For a dangerous situation to arise, there must therefore be two errors:

The unit must initially go into the recirculation stage unintentionally, which may be established easily, and the disinfectant valve must be open by mistake.

Finally, it should be pointed out that the apparatus explained in German Patent Application No. 33 13 421 may be used as the dialysis source 16 for generation of the dialyzing liquid. Express reference is made to the disclosure of this application. In this apparatus, the volume measuring apparatus 54 is advantageously provided in the heating section, in which the line 52 likewise opens out. Thus, the heating section, into which the other feed lines likewise open out, represents the mixing chamber 32 according to the FIGURE.

The invention has been explained with reference to specific embodiments. Other embodiments will be apparent to those of ordinary skill in the art. It is, therefore, not intended that this information be limited except as indicated by the appended claims.

I claim:

1. A hemodialysis apparatus comprising:
   a dialyzer having a membrane, a first chamber, and a second chamber separated from said first chamber by said membrane, said first chamber for coupling into a dialyzing liquid path, and said second chamber for coupling into a blood path;
   a dialyzing liquid source;
   a suction pump disposed in the dialyzing liquid path downstream from the dialyzer for controlling transmembrane pressure in the dialyzer;
   a restrictor means disposed in the dialyzing liquid path upstream of the dialyzer;
   a changeover valve having a first outlet, a second outlet, and an inlet coupled to receive dialyzing liquid downstream from said suction pump;
   a discharge port coupled to said first outlet;
   volume-measuring means for measuring volume of ultrafiltrate liquid;
   means for determining the transmembrane pressure in the dialyzer;
   control means, said control means being coupled at least to the transmembrane pressure determining means for controlling the suction pump in response to transmembrane pressure; and
   a return line coupled to said second outlet of said first changeover valve and connected to the dialyzing liquid source for returning the dialyzing liquid to the dialyzing liquid source in a closed circuit.

2. A hemodialysis apparatus according to claim 1 wherein the dialyzing liquid source includes a mixing chamber and wherein said volume measuring means is coupled to the mixing chamber.

3. A hemodialysis apparatus according to claim 2, wherein said volume-measuring means comprises a riser and further includes a first volume-sensing line coupled from said volume-measuring means to said control means for determining ultrafiltration rate.

4. A hemodialysis apparatus according to claim 2, further including a concentrate container, a concentrate pump and shut-off valve, the shut-off valve being coupled via a freshwater inlet line to a fresh water inlet which is blocked by said shut-off valve during measuring phases under control of said control means via a valve control line, the concentrate pump being coupled via a pump control line to said control means and which is turned off during measuring phases under control of said control means.

5. A hemodialysis apparatus according to claim 2 further including an overflow line from said mixing chamber and an overflow valve in said overflow line, said overflow valve being coupled to said control means via a valve control line and which is blocked under control of said control means during recirculation phases.

6. A hemodialysis apparatus according to claim 1, wherein said volume-measuring means further includes a quantity-counting flow meter coupled via a second volume-sensing line to said control means for determining ultrafiltration rate.

7. A hemodialysis apparatus according to claim 1, further including a set value input means coupled to said control means for providing preselected values to said control means, and wherein said control means is coupled via changeover valve control line to said changeover valve, via a transmembrane pressure control line to said transmembrane pressure determining means, and via a suction pump control line to said suction pump thereby to convert a single-pass-type hemodialysis apparatus into a feedback-controlled recirculating-type hemodialysis apparatus.

* * * * *